United States Patent [19]

Nakanishi

[11] Patent Number: 5,037,299
[45] Date of Patent: Aug. 6, 1991

[54] CHUCKING DEVICE FOR DENTAL HANDPIECE

[75] Inventor: Takasuke Nakanishi, Kanuma, Japan

[73] Assignee: Nakanishi Dental Mfg. Co., Ltd., Tochigi, Japan

[21] Appl. No.: 661,412

[22] Filed: Feb. 26, 1991

[30] Foreign Application Priority Data

Aug. 7, 1990 [JP] Japan ............... 2-207604

[51] Int. Cl.⁵ ............................... A61C 1/14
[52] U.S. Cl. .................................. 433/128
[58] Field of Search ............. 433/126, 127, 128; 279/1 B, 74

[56] References Cited

U.S. PATENT DOCUMENTS

| | | | |
|---|---|---|---|
| 2,911,721 | 11/1959 | Staunt | 433/128 |
| 4,398,886 | 8/1983 | Schuss et al. | 433/128 |
| 4,573,918 | 3/1986 | Bareth | 433/127 |
| 4,661,062 | 4/1987 | Seigneurin | 433/128 |

Primary Examiner—John J. Wilson
Attorney, Agent, or Firm—Charles E. Baxley

[57] ABSTRACT

A chucking device for a dental handpiece includes a dental bur having a retention groove, a stationary disk having a central opening, a pair of locking members having projecting engaging portions for engaging with the reaction groove, a retention spring for thrusting the locking members towards abutment with each other, and a pushbutton for releasing retention of the bur. When the bur is inserted into the central opening, the retention groove is engaged by the projecting engaging portions of the locking members for retaining and securing the bur within a bur tube. When the pushbutton is pressed down, the locking members are extended apart from each other to release the retention of the retention groove by the projecting engaging portions to permit the bur to be disconnected from the inside of the bur tube.

10 Claims, 7 Drawing Sheets

FIG.3
FIG.4
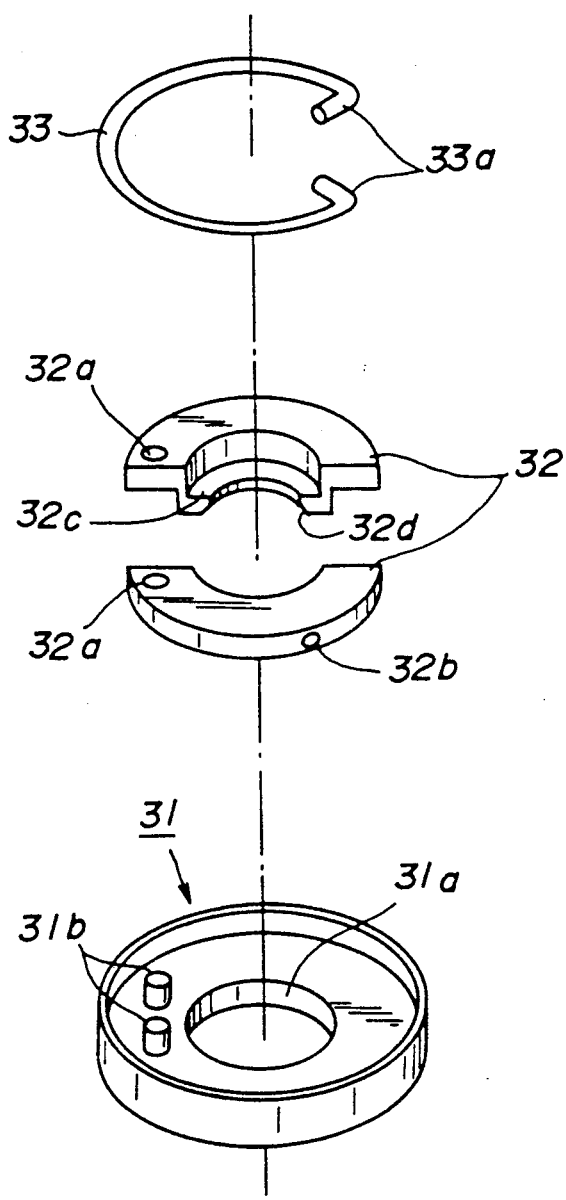
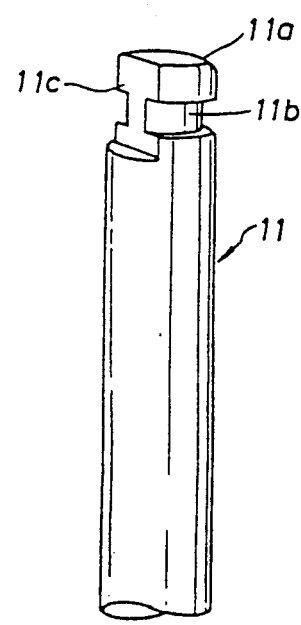

CHUCKING DEVICE FOR DENTAL HANDPIECE

BACKGROUND OF THE INVENTION

This invention relates to a chucking device for a dental handpiece for attaching a dental tool for dental treatment, such as a dental bur, to a head housing.

There are known various types of the chucking devices for the dental handieces, such as, for example, a chucking device described in Japanese Laid-open Patent Publication No. 1-171539 and shown herein in FIGS. 11 and 12.

In these figures, the handpiece shown therein has a foremost section 100 constituted by a head housing 103 for attaching a dental bur 102 and a head housing jacket 101 having its foremost part secured to the head housing 103. A bur tube 104 for receiving and securing the dental bur 102 therein is provided within the head housing 103.

A cover cap 107 having a central opening is fitted over an upper opening 105 of the bur tube 104 and a ring-shaped elastic locking member 106 having a slit 106a is accommodated within the upper opening 105. The elastic locking member 106 may be extended apart at the slit 106a towards both sides with the side thereof opposite to the slit 106a as a fulcrum. A positioning pin 108 implanted inwardly of the fulcrum is used for preventing excess shifting during elastic extension of the locking member 106.

An inclined cam surface 106b is formed at the inner lower end of the locking member 106. When the bur 102 is inserted into the inside of the bur tube 104, an inclined cam surface 102a at an upper engaging projection 102b of the bur 102 abuts on the inclined cam surface 106b of the elastic locking member 106 to extend the elastic locking member 106b apart. On further insertion of the bur 102 into the inside of the bur tube 104, the upper engaging projection 102b is moved past a lower inner step or shoulder 106c of the elastic locking member 106, whereby the elastic locking member 106 is reset to its original position and the projection 102b is engaged with the step 106c to secure the bur 102 within the bur tube 104.

However, in order for the elastic locking member 106 to have a predetermined strength, it is necessary for the elastic locking member 106 to be thicker than a predetermined thickness and, due to such increased thickness, there is but a little space left for the elastic locking member 106 to be extended apart within the bur tube 104. This in turn results in an extremely limited space left for the engaging projection 102b of the bur 102 to be engaged with the step 106c of the elastic locking member 106. Thus, a chucking mechanism has been desired which allows for engagement of the projection 102b of the bur 102 with the step 106c of the locking member 106 within a wider space to permit positive affixture of the bur 102 within the bur tube 104.

SUMMARY OF THE INVENTION

It is a principal object of the present invention to provide a chucking device for a dental handpiece wherein a wider space is allowed for engagement of the proximal part of a dental tool with a locking member to assure a more reliable retention and affixture of the dental tool.

It is another object of the present invention to provide a chucking device for a dental handpiece whereby the dental tool can be reliably secured in position by simply thrusting and pushing the tool into the inside of the handpiece.

It is a further object of the present invention to provide a chucking device for a dental handpiece whereby the dental tool can be quickly detached and removed by a one-touch operation of pushing a pushbutton.

The above and other objects of the present invention will become more apparent from the following description.

In accordance with the present invention, there is provided a chucking device for a dental handpiece comprising a dental tool having a retention groove at the proximal end thereof, a stationary disk having a central opening for passing the dental tool therethrough, a pair of locking members placed on the rim of the central opening of the stationary disk and having projecting engaging portions for engaging with the retention groove of the dental tool, a resilient member for thrusting the locking members into abutment with each other towards substantially the center of the stationary disk, the resilient member operating for engaging and retaining the projecting engaging portions of the locking members into the retention groove of the dental tool to be introduced into the central opening, and a pushbutton for extending the locking members apart from each other against the force of the resilient member for releasing the retention of the dental tool.

BRIEF DESCRIPTION OF THE DRAWINGS

FIG. 3 is an exploded perspective view showing essential parts of the chucking device shown in FIG. 2;

FIG. 4 is a partial perspective view showing the proximal part of a dental bur;

PREFERRED EMBODIMENTS OF THE INVENTION

First referring to FIGS. 1 to 6, a preferred embodiment of the present invention will be explained in detail.

Figure 1:
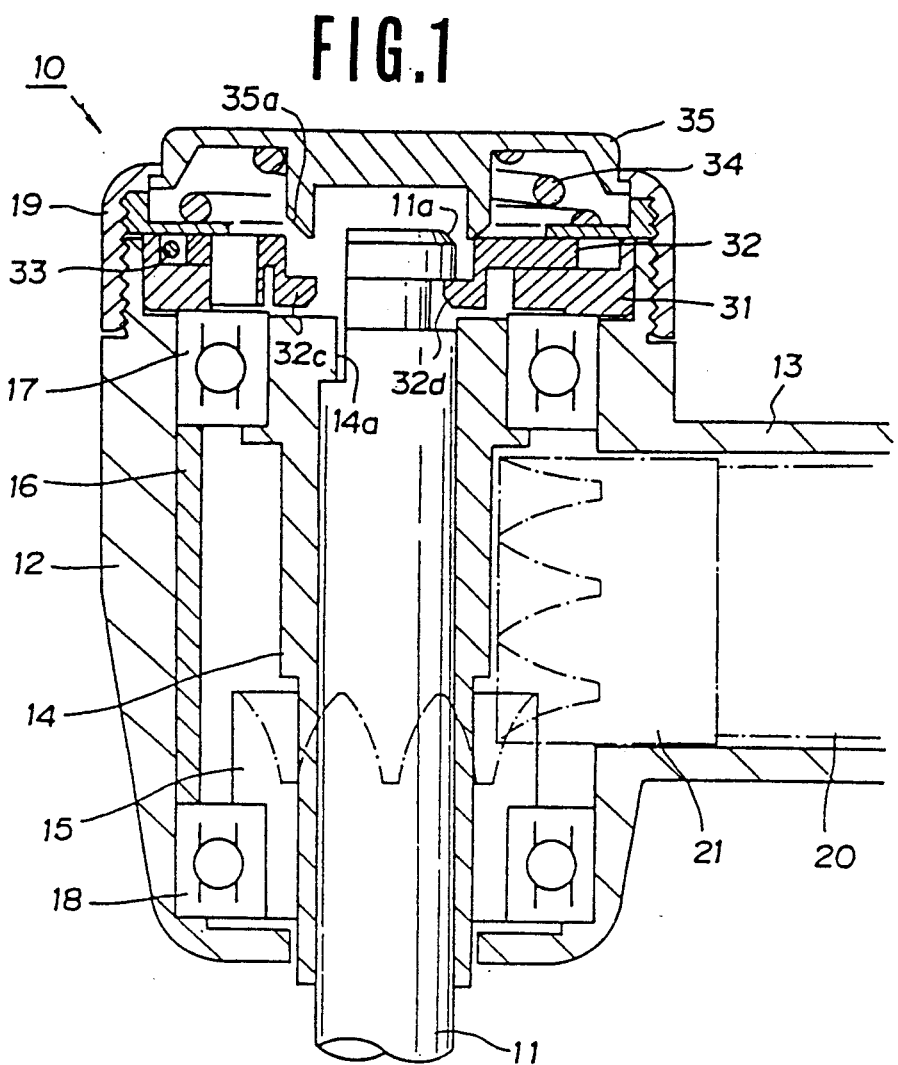
FIG. 1 is a diagrammatic longitudinal cross-sectional view showing the foremost part of a dental handpiece according to the present invention.

Referring to FIG. 1, a foremost section 10 of a dental handpiece includes a head housing 12 for attachment therein of a dental tool, such as a dental bur 11, and a head housing jacket 13. Within the head housing 12, there are provided a bur tube 14 for receiving and securing the bur 11 therein, a head gear 15 for rotating the bur tube 14, and an upper bearing 17 and a lower bearing 18 on both ends of a bearing spacer 16. On the upper end of the head housing 12 is threadedly mounted a head cap 19, in the inside of which a chucking device 30 is mounted for detachably holding the bur 11 in a manner which will be explained subsequently.

A driving shaft 20, rotated by a driving electric motor, not shown, is mounted in the head housing jacket 13, and a driving gear 21 meshing with the head gear 15 for transmitting rotation of the driving shaft 20 to the bur tube 14 is mounted on the distal end of the driving shaft 20.

Figure 2:
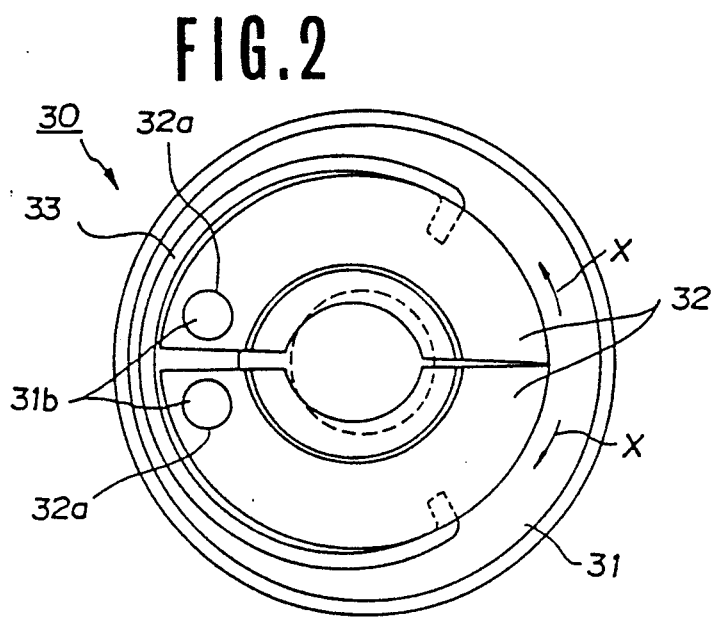
FIG. 2 is a plan view showing an embodiment of a chucking device according to the present invention.

FIGS. 2 and 3 illustrate the chucking device 30 for the dental handpiece of the present invention. The main members of the chucking device 30 include a stationary disk 31 having a central opening 31a for passing the bur 11 therethrough, a pair of locking members 32 each placed around the rim of the central opening 31a and provided with an engaging projecting portion 32c, a substantially C-shaped retention spring 33 for thrusting the locking members 32 towards the center of the stationary disk 31, and a pushbutton 35 for releasing the retention of the bur 11 by the locking members 32.

A pair of positioning pins 31b implanted on the stationary disk 31 are engaged in mating positioning holes 32a formed in the one end of each locking member 32 so that the locking members 32 may be extended apart each other pivotably around the positioning pins 31b in the circumferential direction shown by arrows X in FIG. 2, with the positioning pins 31b as the fulcrum points.

The proximal end of the dental bur 11 is formed with a retention groove 11b for engaging with the engaging projecting portions 32c and an L-shaped flattened surface 11c formed by partially cutting along the longitudinal axis of the bur 11, as shown in FIG. 4. This flattened surface 11c engages with a mating flattened surface 14a at the upper end of the bur tube 14 for preventing the bur 11 from being rotated within the bur tube 14.

The retention spring 33 is placed about the locking members 32 at a position radially outwardly of the positioning pins 31b and has its both end sections 33a engaged in retention holes 32b formed in the rim of the locking members 32 at the positions generally diametrally opposite to the positioning pins 31b. In this manner, the retention spring 33 perpetually thrusts the locking members 32 in the circumferential direction opposite to that shown by the arrows X in FIG. 2.

An inclined cam surface 35a formed on the lower central surface of the pushbutton 35 abuts on the upper inner peripheries of the locking members 32, when the pushbutton 35 is thrust downwards, thereby extending the locking members 32 in a direction away from each other. The pushbutton 35 is perpetually biased to its upper rest position under the force of a coil spring 34.

The operation of attaching and detaching the dental bur 11 to and from the head housing 12 by the chucking device 30 is hereinafter explained.

The proximal end of the bur 11 is first pushed into the inside of the bur tube 14. An inclined cam surface 11a on the rim of the proximal end of the bur 11 then abuts on inclined cam surfaces 32d of the projecting engaging portions 32c of the locking members 32 for extending the locking members 32 apart from each other in the circumferential direction. Thus, the locking members 32 are extended apart from each other in the circumferential direction shown by the arrows X in FIG. 2, with the positioning pins 31b as the fulcrum points. When the bur 11 is thrust further until the retention groove 11b thereof reaches the projecting engaging portions 32c, the locking members 32 are engaged with the retention groove 11b under the force of the retention spring 33 to retain the bur 11 within the bur tube 14, as shown in FIGS. 1 and 2. In this state, the bur 11 cannot be extricated inadvertently from the bur tube 14 so that the bur is rotated along with the bur tube 14.

Figure 5:
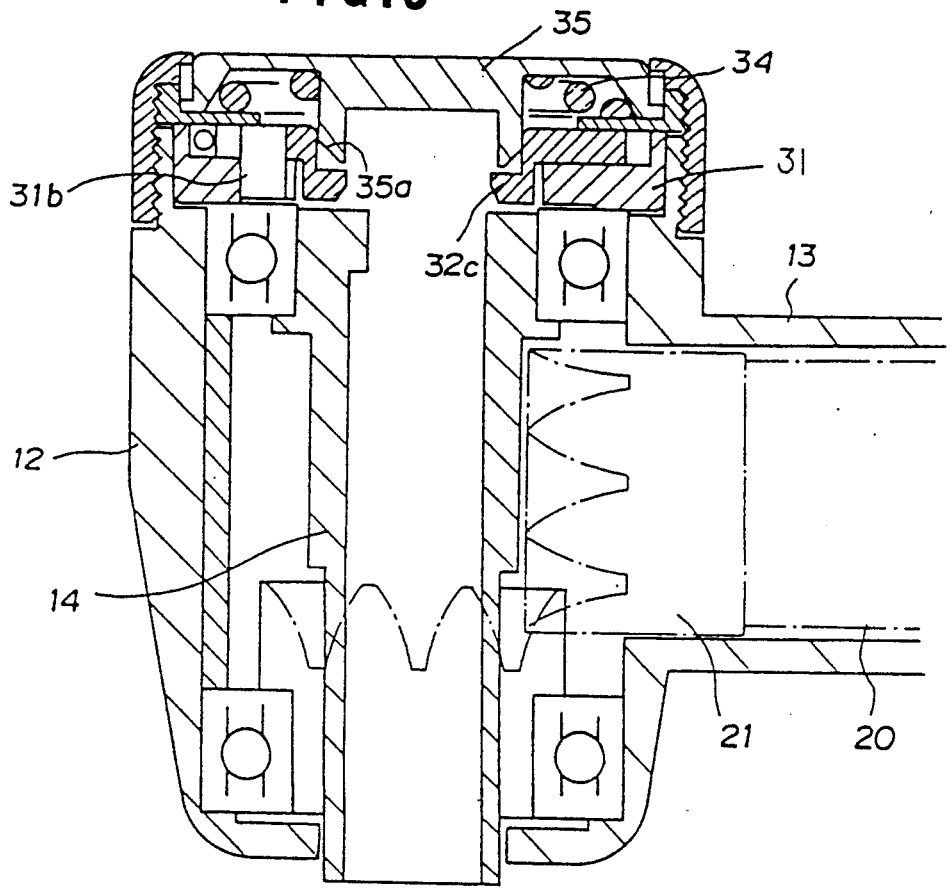
FIG. 5 is a diagrammatic longitudinal cross-sectional view similar to FIG. 1, with the bur having been removed by pushing a pushbutton.
Figure 6:
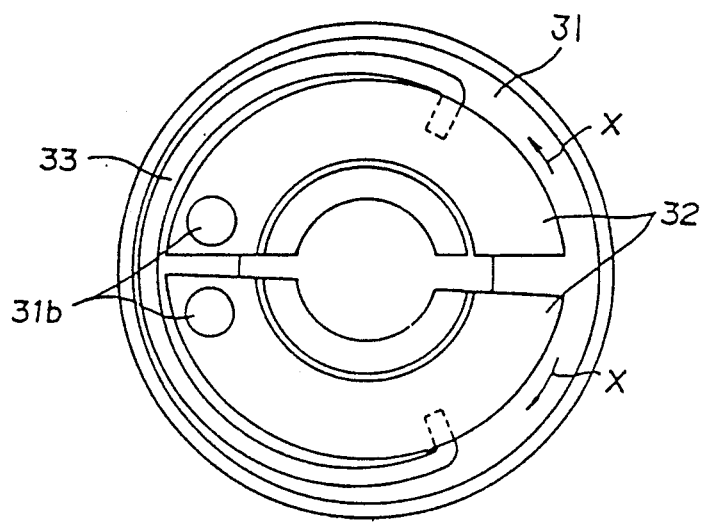
FIG. 6 is a plan view similar to FIG. 2, with the locking members having been extended from the state of FIG. 2 by pushing the pushbutton.

When extracting the dental bur 11 from the head housing 12, the pushbutton 35 is thrust with a finger pressure against the force of the coil spring 34. The inclined cam surface 35a of the pushbutton 35 then abuts on the upper inner peripheries of the locking members 32 to extend the locking members 32 apart from each other in the circumferential direction shown by the arrows X in FIG. 2, with the positioning pins 31b as the fulcrum points, as shown in FIGS. 5 and 6. This releases the retention of the retention groove 11b of the bur 11 by the projecting engaging portions 32c of the locking members 32, so that, when the bur 11 is pulled downwards, it can be extracted easily from the bur tube 14. In this manner, the exchange operation of the bur 11 can be performed easily and quickly.

A modified embodiment of the present invention will be explained by referring to FIGS. 7 to 10. It will be noted that parts or components similar to those of the above described chucking device 30 are indicated by the same reference numerals and the corresponding description is omitted for simplicity.

Figure 9:
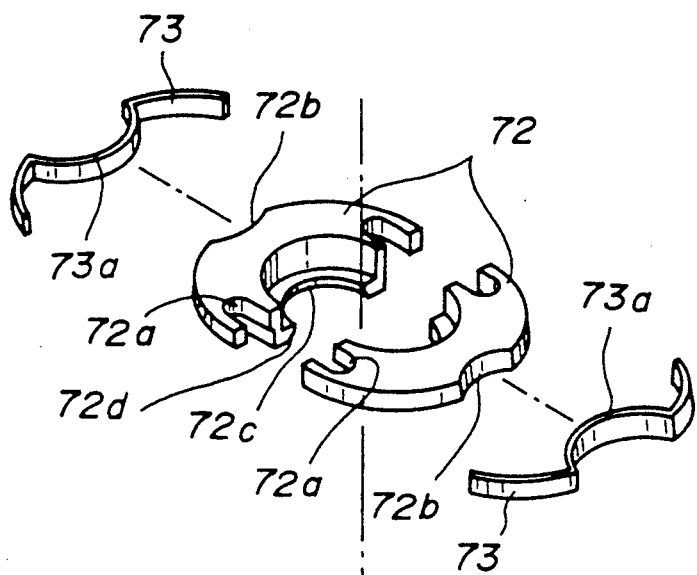
FIG. 9 is an exploded perspective view showing essential parts of the chucking device shown in FIG. 8.
Figure 9:
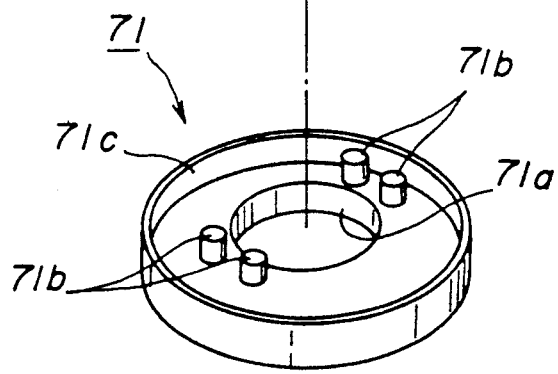
Figure 10:
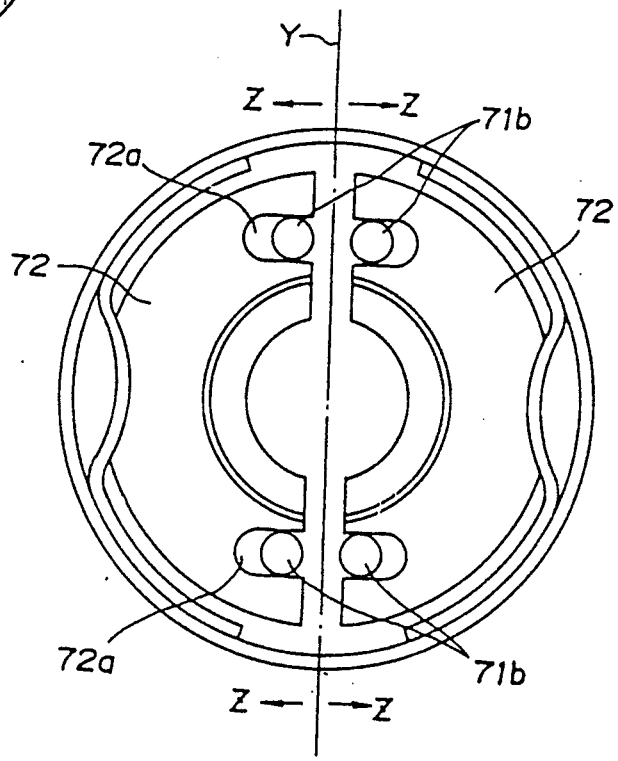
FIG. 10 is a plan view similar to FIG. 8, with the locking members having been extended from the state of FIG. 8 by pushing the pushbutton.
Figure 11:
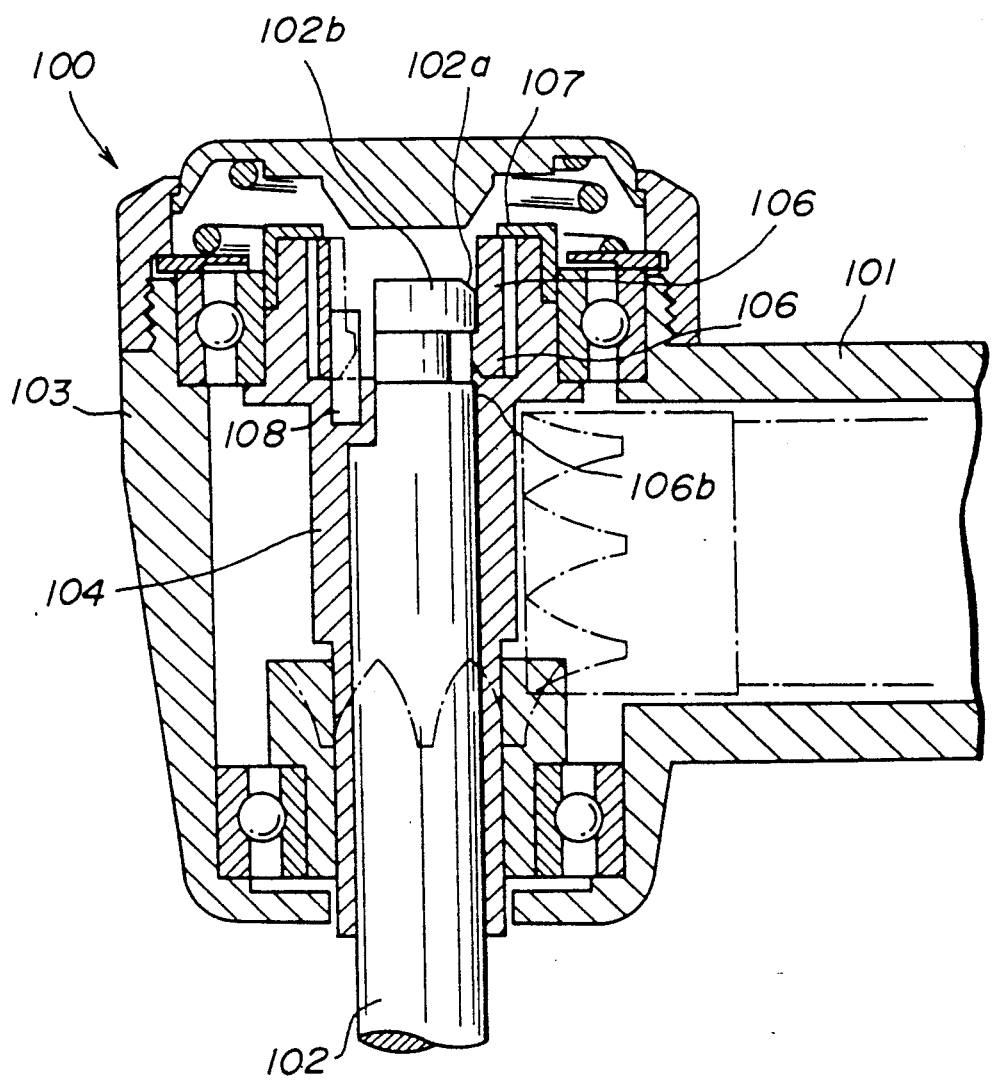
FIG. 11 is a diagrammatic longitudinal cross-sectional view showing the foremost part of a conventional handpiece.
Figure 12:
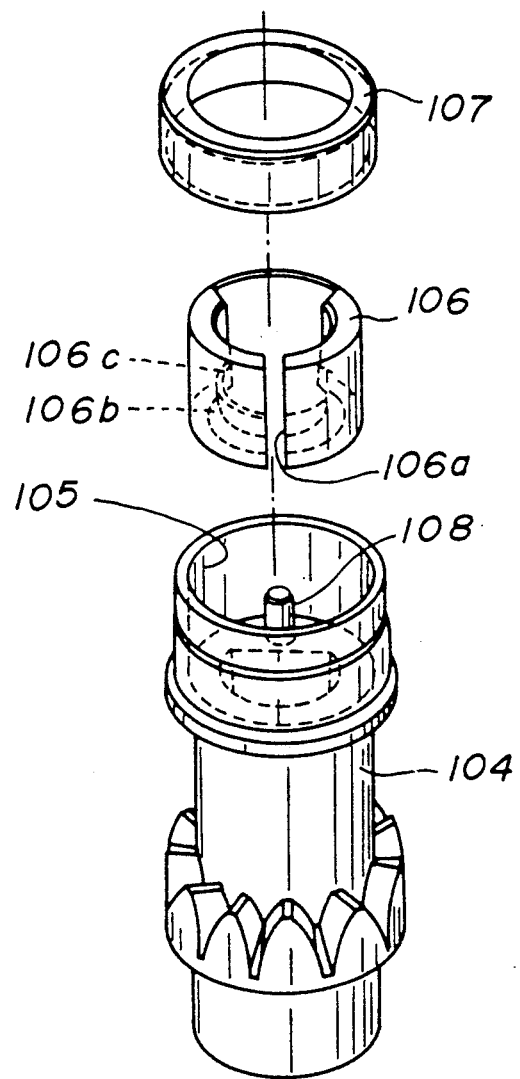
FIG. 12 is an exploded perspective view showing a chucking device employed in the conventional handpiece shown in FIG. 11, with the inner parts of the chucking device being shown for clarity.

Referring to FIG. 9, the main members of a chucking device 70 include a stationary disk 71 having a central opening 71a for passing the dental bur 11 therethrough, a pair of locking members 72 placed around the rim of the central opening 71a and provided with projecting engaging portions 72c, a pair of retention springs 73 for thrusting the locking members 72 from the opposite sides towards the center of the stationary disk 71, and a pushbutton 35 for releasing the bur 11 from the locking members 72.

On the stationary disk 71 are implanted two pairs of positioning pins 71b at the symmetrical positions on both sides along a centerline Y so that the positioning pins 71b are engaged in positioning slots 72a formed in the confronting sides of the locking members 72. In this manner, the locking members 72 may be slid away from each other in the direction at right angles to the centerline Y, that is, in the direction shown by arrows Z therein, while the locking members 72 are guided by the positioning pins 71b.

Each retention spring 73 is in the form of a flattened letter M and has its arcuate end sections engaging with the periperal wall 71c of the stationary disk 71 so that its central inversely arcuate section 73a abuts on a mating arcuate recess 72b of the locking member 72. In this manner, the retention springs 73 perpetually thrust the locking members 72 towards the centerline Y.

The operation of attaching and detaching the dental bur 11 to and from the head housing 12 by the chucking device 70 is hereinafter explained.

Figure 7:
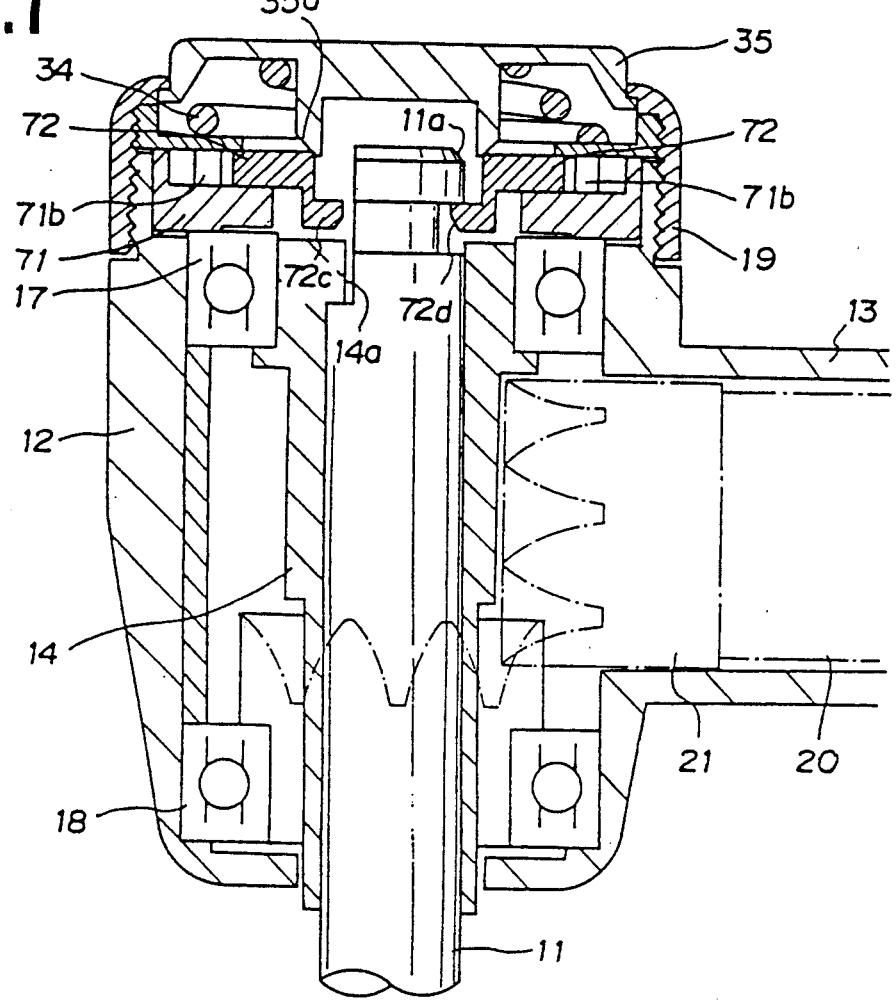
FIG. 7 is a longitudinal cross-sectional view of a dental handpiece according to a modified embodiment of the present invention.
Figure 8:
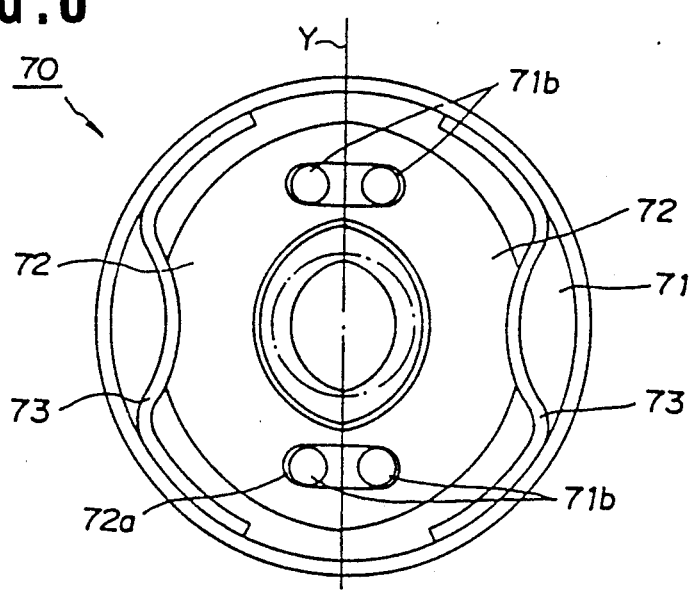
FIG. 8 is a plan view showing a chuck device employed in the dental handpiece shown in FIG. 7.

The proximal end of the bur 11 is first pushed into the inside of the bur tube 14. The inclined cam surface 11a on the rim of the proximal end of the bur 11 then abuts on inclined cam surfaces 72d of the projecting engaging portions 72c of the locking members 72 for extending the locking members 72 apart from each other. Thus, the locking members 72 are moved away from both sides of the centerline Y, as shown by arrows Z in FIG. 10, while the locking members 72 are guided by the positioning pins 71b. When the bur 11 is thrust further until the retention groove 11b thereof reaches the projecting engaging portions 72c, the locking members 72 are engaged with the retention groove 11b under the force of the retention springs 73, thereby retaining the bur 11 within the bur tube 14 as shown in FIGS. 7 and 8. In this state, the bur 11 cannot be extricated inadvertently from the bur tube 14 so that the bur is rotated along with the bur tube 14.

When extracting the dental bur 11 from the head housing 12, the pushbutton 35 is thrust with a finger pressure against the force of the coil spring 34. The inclined cam surface 35a of the pushbutton 35 then abuts on the upper inner peripheries of the locking members 32 to extend the locking members 72 apart from each other. Thus, the locking members 72 are again moved in the direction away from both sides of the centerline Y in FIG. 10, as shown by the arrows Z shown therein, while the locking members 72 are guided by the positioning pins 71b. This releases the retention of the bur 11 by the projecting engaging portions 72c of the locking members 72, so that, when the bur 11 is withdrawn downwards, it can be extricated from the head housing 12.

Although the present invention has been described with reference to the preferred embodiments, it should be understood that various modifications and variations can be easily made by those skilled in the art without departing from the spirit of the invention. Accordingly, the foregoing disclosure should be interpreted as illustrative only and is not to be interpreted in a limiting sense. The present invention is limited only by the scope of the following claims.

What is claimed is:

1. A chucking device for a dental handpiece comprising
    a dental tool having a retention groove at a proximal end thereof,
    a stationary disk having a central opening for passing said dental tool therethrough,
    a pair of locking members placed on a rim of said central opening of said stationary disk and having projecting engaging portions for engaging with said retention groove of said dental tool,
    a resilient member for thrusting said locking members into abutment with each other towards substantially the center of said stationary disk, said resilient member operating for engaging and retaining said projecting engaging portions of said locking members into said retention groove of said dental tool to be introduced into said central opening, and
    a pushbutton for extending said locking members apart from each other against force of said resilient member for releasing retention of said dental tool.

2. The chucking device according to claim 1 wherein a pair of positioning holes is formed in said locking members and a pair of positioning pins implanted on said stationary disk is engaged in said positioning holes so that said locking members are extended apart from each other in a circumferential direction with said positioning pins functioning as a fulcrum.

3. The chucking device according to claim 1 wherein said resilient member comprises a ring-shaped spring member for resiliently holding said locking members therebetween.

4. The chucking device according to claim 1 wherein at least one positioning slot is formed in each of said locking members and wherein positioning pins implanted on said stationary disk are engaged in said positioning slots so that said locking members are slid in a direction away from each other while being guided by said positioning pins.

5. The chucking device according to claim 4 wherein said resilient member comprises a pair of spring members thrustingly engaged with a peripheral wall of said stationary disk and thrusting said locking members towards substantially the center of said disk.

6. The chucking device according to claim 4 wherein said spring members each include a projecting section projecting towards the center of said stationary disk, each of said projecting sections being engaged in a mating arcuate recess formed on an outer periphery of each of said locking members.

7. The chucking device according to claim 1 wherein said resilient member comprises a pair of spring members thrustingly engaged with a peripheral wall of said stationary disk and thrusting said locking members towards substantially the center of said disk.

8. The chucking device according to claim 7 wherein said spring members each include a projecting section projecting towards the center of said stationary disk, each of said projecting sections being engaged in a mating arcuate recess formed on an outer periphery of each of said locking members.

9. The chucking device according to claim 1 wherein a cam surface abutting on a proximal end of said dental tool are formed at lower ends of said locking members.

10. The chucking device according to claim 1 wherein a cam surface abutting on said locking members is formed at a lower end of said pushbutton.

* * * * *